US00PP23688P2

(12) United States Plant Patent
Bradford

(10) Patent No.: US PP23,688 P2
(45) Date of Patent: Jun. 25, 2013

(54) INTERSPECIFIC TREE NAMED 'PLUMRED VII'

(50) Latin Name: ***Prunus* sp.**
Varietal Denomination: Plumred VII

(76) Inventor: Lowell Glen Bradford, Le Grand, CA (US)

( * ) Notice: Subject to any disclaimer, the term of this patent is extended or adjusted under 35 U.S.C. 154(b) by 62 days.

(21) Appl. No.: 13/374,014

(22) Filed: Dec. 8, 2011

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP21,051 P2 6/2010 Bradford

*Primary Examiner* — Annette Para

(57) ABSTRACT

The present invention relates to an interspecific tree and more particularly to a new and distinct variety broadly characterized by a medium size, vigorous, hardy, and productive tree. Being self-unfruitful, the present variety requires cross pollination from an apricot, interspecific, or plum that blooms during the mid to late season. The present variety produces a heavy bloom with an abundant amount of pollen to entice good bee activity to facilitate pollination. The fruit matures under the ecological conditions described during the last half of July, with first picking on Jul. 23, 2011, and can hang on the tree for up to thirty days. The fruit is uniformly large in size, dark red in skin color, clingstone in type, globose in shape, dark red in flesh color, firm in texture, and excellent flavor.

1 Drawing Sheet

Botanical classification: *Prunus* sp.
Varietal denomination: 'PLUMRED VII'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree which has been denominated varietally as 'Plumred VII'.

During a typical blooming season I isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2003 one such house containing an unpatented red plum, code named '19P442', was crossed by me in this manner. To pollinate this red plum, I selected bouquets from several sources of apricot and interspecific hybrid trees without keeping specific written details. Upon reaching maturity the fruit from this red plum tree was harvested and the seeds were removed, cracked, stratified and germinated as a group with the label "H5". They were grown as seedlings on their own root in my greenhouse and upon reaching dormancy transplanted to a cultivated area of my experimental orchard located near Le Grand, Calif. in Merced County (San Joaquin Valley). During the summer of 2007 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, '19P442' plum (unpatented), by being self-unfruitful and by producing fruit that is full dark red to purple in skin color, full red in flesh color, and firm in texture, but is distinguished therefrom by producing fruit that is larger in size, that is much sweeter in flavor, and that matures about twenty days later.

The present variety is most similar to 'Plumred VI' (U.S. Plant Pat. No. 21,051) interspecific tree, by being self-unfruitful and by producing fruit that is large in size, globose in shape, firm, juicy, and sweet in flavor, but is distinguished therefrom by blooming about six days earlier and by producing fruit that is darker red in skin color, that is somewhat darker red in flesh color, and that ripens about four days earlier, but has a much longer picking window because it can hang on the tree for up to thirty days.

SUMMARY OF VARIETY

The present interspecific variety is characterized by a medium size, vigorous, hardy, and productive tree. Being self-unfruitful, the present variety requires cross pollination from an apricot, interspecific, or plum that blooms during the mid to late season. The present variety produces a heavy bloom with an abundant amount of pollen to entice good bee activity to facilitate pollination. The fruit matures under the ecological conditions described during the last half of July, with first picking on Jul. 23, 2011, and can hang on the tree for up to thirty days. The fruit is uniformly large in size, dark red in skin color, clingstone in type, globose in shape, dark red in flesh color, firm in texture, and excellent flavor.

DRAWING

The accompanying photograph consists of four whole fruits positioned to display the characteristics of the skin color and form, a half fruit divided to reveal the flesh and stone, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Jul. 29, 2011, on the original tree during its eighth growing season. The flower and bud descriptions were developed during the previous blooming season. All major color code designations are by reference to the Inter-Society Color Council, National Bureau of Standards. Common color names are also used occasionally.

PARENTAGE

Seed parent: '19P442' plum (unpatented).
Pollen parent: Unknown.

TREE

Size: Medium, reaching a height of 10' [3.05 m.] and a spread of 7' [2.13 m.] after eight growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Central leader.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid to late seasonal blooming apricot, interspecific, or plum, such as 'Blackred XII' (U.S. Plant Pat. No. 20,892) interspecific tree.

Bearing: Regular bearer, with no crop failures observed.

Trunk:

- *Size*.—Medium, reaching a maximum diameter of 5" [127 mm.] after the eighth growing season.
- *Texture*.—Medium shaggy.
- *Bark color*.—A Dark grayish brown [62. d.gy.Br] and Dark brown [59. d.Br] variegation with Deep orange yellow [69. deep OY] crevices present.
- *Lenticels*.—Approximate Number Per Square Inch: 6. Color: Strong orange [50. s.O]. Average Size: ¼" [6.4 mm.]. Shape: Elongated, eye-shaped.

Branches:

- *Size*.—Diameter of the scaffold is 4" [101.6 mm.] measured 12" above the first hanger. Diameter of first hanger is ¾" [19.1 mm.].
- *Texture*.—Smooth on first year wood, increasing roughness with age.
- *Color*.—1st Year Wood Topside: Grayish red [19. gy.R]. 1st Year Wood Underside: Brilliant yellow green [116. brill.YG]. 2nd Year Wood: Strong brown [55. s.Br] with Light yellowish brown [76. l.yBr] crevices and Strong yellow green [117.s.YG] permeating through from underneath.
- *Lenticels*.—Number Per Square Inch: Approximately 40 on second year wood. Color: Light yellowish brown [76. l.yBr]. Size: 1/64" [0.4 mm.] to 1/16" [1.6 mm.]. Shape: Eye-shaped.

Leaves:

- *Size*.—Medium. Average Length: 3⅜" [85.7 mm.]. Average Width: 1⅞" [47.6 mm.].
- *Arrangement*.—Alternate.
- *Thickness*.—Medium.
- *Form*.—Elliptical.
- *Apex*.—Acuminate.
- *Base*.—Acute with an average angle base angle of 80 degrees.
- *Surface*.—Smooth.
- *Color*.—Dorsal Surface: Very dark yellowish green [138. v.d.yG]. Ventral Surface: Dark yellowish green [137. d.yG].
- *Margin*.—Finely serrate.
- *Venation*.—Pinnately net veined.
- *Petiole*.—Average Length: 7/16" [11.1 mm.]. Average Thickness: 1/16" [1.6 mm.]. Color: Brilliant yellow green [116. brill.YG], often Grayish red [19. gy.R] where exposed to direct sunlight.
- *Stipules*.—Number: 2 per leaf at young stage, up to 6 per growing tip. Average Length: 5/16" [7.9 mm.]. Color: Brilliant yellow green [116. brill.YG] becoming Moderate reddish brown [43. m.rBr] with age.
- *Glands*.—Number: Mostly 2 per leaf. Position: Alternately positioned at the intersection of the petiole and the leaf blade. Size: Small. Form: Globose. Color: Light yellow green [119. l.YG] becoming Grayish reddish brown [46. gy.rBr] with age.
- *Leaf buds*.—Pointed, medium.

Flower buds:

- *Hardiness*.—Hardy, with respect to central California winters.
- *Diameter*.—Typically 3/16" [4.8 mm.] 1 week before bloom.
- *Length*.—Typically ⅜" [9.5 mm.] 1 week before bloom.
- *Form*.—Not appressed.
- *Surface*.—Pubescent.
- *Tip color*.—White [263. White] with some Moderate Pink [5. m.Pk] tinging.

Flowers: Perfect, complete, perigynous, usually a single pistil, typically thirty or more stamens, five sepals and petal locations alternately positioned.

- *Average flower diameter*.—1⅛" [28.6 mm.].
- *Number of petals*.—Five, no double blossoms observed.
- *Petal shape*.—Oval to circular.
- *Petal margin*.—Entire, wavy.
- *Average petal diameter*.—½" [12.7 mm.].
- Average petal length.—⅝" [15.9 mm.].
- *Petal apex*.—Rounded.
- *Petal base*.—Obtuse.
- *Petal color*.—White [263. White] on both sides.
- *Anther color*.—Very yellow [82. v.Y].
- *Stigma color*.—Light greenish yellow [101. l.gY].
- *Sepal color*.—Brilliant yellow green [116 brill.YG] on the outer surface.
- *Sepal length*.—7/32" [5.6 mm.].
- *Sepal width*.—3/16" [4.8 mm.].

*Sepal apex*.—Rounded to elliptical to match the width and length.
*Sepal margin*.—Fairly smooth to the naked eye, slightly serrated when magnified.
*Average pistil length*.—9/16" [14.3 mm.].
*Average stamen length*.—½" [12.7 mm.].
*Fragrance*.—Moderate.
*Pollen production*.—Heavy, very bee enticing.
*Blooming period*.—Mid to late, with 'September Yummy®' plum (U.S. Plant Pat. No. 14,220).
*Onset of bloom*.—One percent on Mar. 2, 2011.
*Date of full bloom*.—Mar. 11, 2011.
*Duration of bloom*.—One to two weeks, dependent on ambient temperature.
*Bloom density*.—Heavy.
*Number per cluster*.—2 to 9, average 4.

FRUIT

Maturity when described: Firm ripe, Jul. 29, 2011.
Date of first picking: Jul. 23, 2011.
Date of last picking: Aug. 21, 2011.
Size: Uniform, Large.
*Average diameter axially*.—2 7/16" [61.9 mm.].
*Average diameter across cheek plane*.—2 9/16" [65.1 mm.].
*Average diameter across suture plane*.—2½" [63.5 mm.].
*Typical weight*.—5.9 ounces [167 grams].
Form: Uniform, globose, mostly symmetrical.
*Longitudinal section form*.—Oval.
*Transverse section through diameter*.—Circular to elliptical.
Suture: An indistinct line located in a shallow groove extending from the base just to the apex.
Ventral surface: Rounded, lightly lipped throughout on both sides.
Lips: Slightly unequal.
Cavity: Flaring, circular, suture showing on one side.
*Depth*.—7/16" [11.1 mm.].
*Breadth*.—1 3/16" [30.2 mm.].
Base: Truncate, slightly cordate if viewed parallel to the suture.
Apex: Rounded.
Pistil point: An inconspicuous dot.
Stem: Medium.
*Average length*.—9/16" [14.3 mm.].
*Average width*.—1/16" [1.6 mm.].
Skin:
*Thickness*.—Medium.
*Surface*.—Smooth.
*Tenacity*.—Tenacious to the flesh.
*Astringency*.—Slight.
*Tendency to crack*.—Slight in wet seasons.
*Color*.—Very dark red [17. v.d.R] covered with heavy Dark greenish yellow [103. d.gY] freckling throughout.
*Bloom*.—Moderate.
Flesh:
*Color*.—Very dark red [17. v.d.R] toward the skin smoothly blending to Moderate red [15. m.R] toward the stone.
*Surface of pit cavity*.—Covered with Dark red [16. d.R] broken fibers when twisted away from stone.
*Amygdalin*.—Moderate.
*Juice*.—Abundant, rich.
*Texture*.—Firm, crisp, meaty.
*Fibers*.—Abundant.
*Ripens*.—Fairly even, slightly earliest at apex.
*Flavor*.—A tasty blend of acid and sugar, typically 21 brix.
*Aroma*.—Very slight.
*Eating quality*.—Excellent.

STONE

Type: Clingstone.
Form: Oval.
Hilum: Narrow, oval.
Base: Rounded, slightly truncate.
Apex: Obtuse with a very short and sharp prong at the tip.
Sides: Equal.
Surface: Rough throughout.
External color of stone: Light yellowish brown [76. l.yBr] when first removed.
Pit wall color when cracked: Light yellowish brown [76. l.yBr].
Cavity surface color: Strong yellowish brown [74. s.yBr].
Average pit wall thickness: 1/16" [1.6 mm.].
Average width: ⅝" [15.9 mm.].
Average length: 13/16" [20.6 mm.].
Average breadth: ⅜" [9.5 mm.].
Tendency to split: None observed.
Kernel:
*Form*.—Oval.
*Skin color*.—Pale yellow [89. p.Y] when first removed.
*Pellicle color*.—Dark grayish yellow [91. d.gy.Y].
*Vein color*.—Dark orange yellow [72. d.OY].
*Taste*.—Bitter.
*Viable*.—Yes.
*Average width*.—7/16" [11.1 mm.].
*Average length*.—9/16" [14.3 mm.].
*Amygdalin*.—Moderate.

USE

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is most similar to 'Plumred VI' (U.S. Plant Pat. No. 21,051) interspecific tree, by being self-unfruitful and by producing fruit that is large in size, globose in shape, firm, juicy, and sweet in flavor, but is distinguished therefrom by blooming about six days earlier and by producing fruit that is darker red in skin color, that is somewhat darker red in flesh color, and that ripens about four days earlier, but has a much longer picking window because it can hang on the tree for up to thirty days.

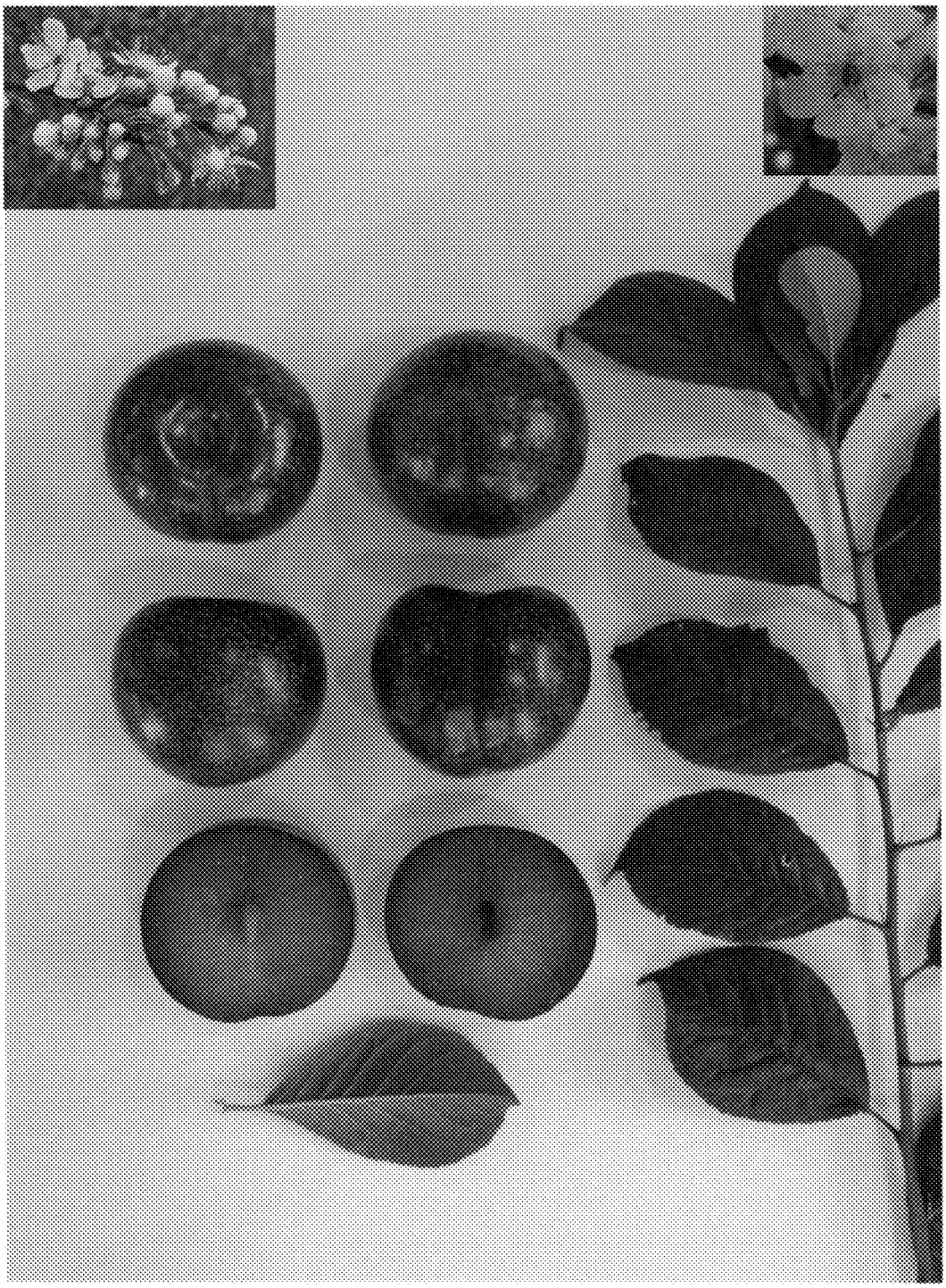

* * * * *